(12) United States Patent
Maschino et al.

(10) Patent No.: US 8,483,846 B2
(45) Date of Patent: Jul. 9, 2013

(54) MULTI-ELECTRODE ASSEMBLY FOR AN IMPLANTABLE MEDICAL DEVICE

(75) Inventors: Steven E. Maschino, Seabrook, TX (US); Bryan P. Byerman, League City, TX (US)

(73) Assignee: Cyberonics, Inc., Houston, TX (US)

( * ) Notice: Subject to any disclaimer, the term of this patent is extended or adjusted under 35 U.S.C. 154(b) by 452 days.

(21) Appl. No.: 12/757,002

(22) Filed: Apr. 8, 2010

(65) Prior Publication Data

US 2010/0192374 A1     Aug. 5, 2010

Related U.S. Application Data

(62) Division of application No. 11/494,057, filed on Jul. 26, 2006, now abandoned.

(51) Int. Cl.
*A61N 1/05*     (2006.01)

(52) U.S. Cl.
USPC ............ 607/118; 607/116; 607/127; 607/131

(58) Field of Classification Search
USPC .................. 607/116, 118, 127, 131
See application file for complete search history.

(56) References Cited

U.S. PATENT DOCUMENTS

| | | |
|---|---|---|
| 3,421,511 A | 1/1969 | Schwartz et al. |
| 3,760,812 A | 9/1973 | Timm et al. |
| 3,796,221 A | 3/1974 | Hagfors |
| 4,291,699 A | 9/1981 | Geddes et al. |
| 4,305,402 A | 12/1981 | Katims |
| 4,384,926 A | 5/1983 | Wagner |
| 4,407,303 A | 10/1983 | Akerstrom |
| 4,458,696 A | 7/1984 | Larimore |
| 4,459,989 A | 7/1984 | Borkan |
| 4,573,481 A | 3/1986 | Bullara |
| 4,590,946 A | 5/1986 | Loeb |
| 4,592,359 A | 6/1986 | Galbraith |
| 4,606,349 A | 8/1986 | Livingston et al. |
| 4,608,985 A | 9/1986 | Crish et al. |

(Continued)

FOREIGN PATENT DOCUMENTS

| | | |
|---|---|---|
| DE | 197 50 043 A1 | 5/1999 |
| EP | 1 790 380 A1 | 5/2007 |

(Continued)

OTHER PUBLICATIONS

J. Walter Woodbury and Dixon M. Woodbury, Vagal Stimulation Reduces the Severity of Maximal Electroshock Seizures in Intact Rates: Use of a Cuff Electrode for Stimulating and Recording, Department of Physiology, School of Medicine, University of Utah, Jan. 1991, pp. 94-107, vol. 14, Salt Lake City, Utah.

(Continued)

*Primary Examiner* — Joseph Dietrich
(74) *Attorney, Agent, or Firm* — Cyberonics, Inc.

(57) ABSTRACT

A method, system, and apparatus are provided for an electrode assembly comprising a plurality of electrodes for use with an implantable medical device for conducting an electrical signal between the implantable medical device and a target tissue. The electrode assembly includes a helical member and first and second electrodes formed upon the helical member. The first and second electrodes are adapted to deliver the electrical signal. The electrode assembly also includes a first conductive element formed upon the helical member and operatively coupled to the first electrode. The electrode assembly also includes a second conductive element formed upon the helical member and operatively coupled to the second electrode.

24 Claims, 8 Drawing Sheets

U.S. PATENT DOCUMENTS

| | | |
|---|---|---|
| 4,612,934 A | 9/1986 | Borkan |
| 4,628,942 A | 12/1986 | Sweeney et al. |
| 4,630,615 A | 12/1986 | Yomtov |
| 4,649,936 A | 3/1987 | Ungar et al. |
| 4,702,254 A | 10/1987 | Zabara |
| 4,793,353 A | 12/1988 | Borkan |
| 4,821,724 A | 4/1989 | Whigham et al. |
| 4,827,932 A | 5/1989 | Ideker et al. |
| 4,850,356 A | 7/1989 | Heath |
| 4,860,616 A | 8/1989 | Smith |
| 4,867,164 A | 9/1989 | Zabara |
| 4,870,341 A | 9/1989 | Pihl et al. |
| 4,899,750 A | 2/1990 | Ekwall |
| 4,903,700 A | 2/1990 | Whigham et al. |
| 4,920,979 A | 5/1990 | Bullara |
| 4,964,407 A | 10/1990 | Baker, Jr. et al. |
| 4,969,468 A | 11/1990 | Byers et al. |
| 4,979,511 A | 12/1990 | Terry, Jr. |
| 5,003,975 A | 4/1991 | Hafelfinger et al. |
| 5,025,807 A | 6/1991 | Zabara |
| 5,095,905 A | 3/1992 | Klepinski |
| 5,111,815 A | 5/1992 | Mower |
| 5,137,020 A | 8/1992 | Wayne et al. |
| 5,137,021 A | 8/1992 | Wayne et al. |
| 5,139,028 A | 8/1992 | Steinhaus et al. |
| 5,146,920 A | 9/1992 | Yuuchi et al. |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,201,808 A | 4/1993 | Steinhaus et al. |
| 5,201,865 A | 4/1993 | Kuehn |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,237,991 A | 8/1993 | Baker, Jr. et al. |
| 5,251,634 A | 10/1993 | Weinberg |
| 5,263,480 A | 11/1993 | Wernicke et al. |
| 5,269,303 A | 12/1993 | Wernicke et al. |
| 5,282,468 A | 2/1994 | Klepinski |
| 5,299,569 A | 4/1994 | Wernicke et al. |
| 5,304,206 A | 4/1994 | Baker, Jr. et al. |
| 5,324,322 A | 6/1994 | Grill, Jr. et al. |
| 5,330,515 A | 7/1994 | Rutecki et al. |
| 5,335,657 A | 8/1994 | Terry, Jr. et al. |
| 5,351,394 A | 10/1994 | Weinberg |
| 5,411,528 A | 5/1995 | Miller et al. |
| 5,431,692 A | 7/1995 | Hansen et al. |
| 5,466,255 A | 11/1995 | Franchi |
| 5,501,702 A | 3/1996 | Plicchi et al. |
| 5,507,786 A | 4/1996 | Morgan et al. |
| 5,522,865 A | 6/1996 | Schulman et al. |
| 5,531,778 A | 7/1996 | Maschino et al. |
| 5,534,018 A | 7/1996 | Wahlstrand et al. |
| 5,540,730 A | 7/1996 | Terry, Jr. et al. |
| 5,540,734 A | 7/1996 | Zabara |
| 5,549,646 A | 8/1996 | Katz et al. |
| 5,571,150 A | 11/1996 | Wernicke et al. |
| 5,575,813 A | 11/1996 | Edell et al. |
| 5,620,474 A | 4/1997 | Koopman |
| 5,658,318 A | 8/1997 | Stroetmann et al. |
| 5,689,877 A | 11/1997 | Grill, Jr. et al. |
| 5,690,681 A | 11/1997 | Geddes et al. |
| 5,700,282 A | 12/1997 | Zabara |
| 5,707,400 A | 1/1998 | Terry, Jr. et al. |
| 5,713,936 A | 2/1998 | Staub et al. |
| 5,720,099 A | 2/1998 | Parker et al. |
| 5,741,311 A | 4/1998 | Mc Venes et al. |
| 5,743,860 A | 4/1998 | Hively et al. |
| 5,755,742 A | 5/1998 | Schuelke et al. |
| 5,755,747 A | 5/1998 | Daly et al. |
| 5,759,199 A | 6/1998 | Snell et al. |
| 5,769,873 A | 6/1998 | Zadeh |
| 5,796,044 A | 8/1998 | Cobian et al. |
| 5,814,088 A | 9/1998 | Paul et al. |
| 5,876,425 A | 3/1999 | Gord et al. |
| 5,891,179 A | 4/1999 | Er et al. |
| 5,897,577 A | 4/1999 | Cinbis et al. |
| 5,916,239 A | 6/1999 | Geddes et al. |
| 5,919,220 A | 7/1999 | Stieglitz et al. |
| 5,928,272 A | 7/1999 | Adkins et al. |
| 5,995,868 A | 11/1999 | Osorio et al. |
| 6,035,237 A | 3/2000 | Schulman et al. |
| 6,052,624 A | 4/2000 | Mann |
| 6,073,050 A | 6/2000 | Griffith |
| 6,104,956 A | 8/2000 | Naritoku et al. |
| 6,154,678 A | 11/2000 | Lauro |
| 6,171,239 B1 | 1/2001 | Humphrey |
| 6,181,969 B1 | 1/2001 | Gord |
| 6,208,902 B1 | 3/2001 | Boveja |
| 6,212,431 B1 | 4/2001 | Hahn et al. |
| 6,216,045 B1 | 4/2001 | Black et al. |
| 6,259,951 B1 | 7/2001 | Kuzma et al. |
| 6,269,270 B1 | 7/2001 | Boveja |
| 6,304,787 B1 | 10/2001 | Kuzma et al. |
| 6,317,633 B1 | 11/2001 | Jorgenson et al. |
| 6,339,725 B1 | 1/2002 | Naritoku et al. |
| 6,341,236 B1 | 1/2002 | Osorio et al. |
| 6,393,325 B1 | 5/2002 | Mann et al. |
| 6,400,988 B1 | 6/2002 | Gurewitsch |
| 6,418,348 B1 | 7/2002 | Witte |
| 6,445,951 B1 | 9/2002 | Mouchawar |
| 6,453,198 B1 | 9/2002 | Torgerson et al. |
| 6,456,481 B1 | 9/2002 | Stevenson |
| 6,473,653 B1 | 10/2002 | Schallhorn et al. |
| 6,477,417 B1 | 11/2002 | Levine |
| 6,490,486 B1 | 12/2002 | Bradley |
| 6,505,074 B2 | 1/2003 | Boveja et al. |
| 6,510,332 B1 | 1/2003 | Greenstein |
| 6,529,774 B1 | 3/2003 | Greene |
| 6,553,263 B1 | 4/2003 | Meadows et al. |
| 6,556,868 B2 | 4/2003 | Naritoku et al. |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,600,957 B2 | 7/2003 | Gadsby |
| 6,606,523 B1 | 8/2003 | Jenkins |
| 6,609,025 B2 | 8/2003 | Barrett et al. |
| 6,620,186 B2 | 9/2003 | Saphon et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,648,823 B2 | 11/2003 | Thompson |
| 6,658,294 B1 | 12/2003 | Zadeh et al. |
| 6,662,053 B2 | 12/2003 | Borkan |
| 6,671,556 B2 | 12/2003 | Osorio et al. |
| 6,684,105 B2 | 1/2004 | Cohen et al. |
| 6,687,538 B1 | 2/2004 | Hrdlicka et al. |
| 6,690,974 B2 | 2/2004 | Archer et al. |
| 6,711,440 B2 | 3/2004 | Deal et al. |
| 6,718,203 B2 | 4/2004 | Weiner et al. |
| 6,718,207 B2 | 4/2004 | Connelly |
| 6,721,600 B2 | 4/2004 | Jorgenson et al. |
| 6,721,603 B2 | 4/2004 | Zabara et al. |
| 6,725,092 B2 | 4/2004 | MacDonald et al. |
| 6,731,979 B2 | 5/2004 | MacDonald |
| 6,745,077 B1 | 6/2004 | Griffith et al. |
| 6,754,539 B1 | 6/2004 | Erickson et al. |
| 6,757,566 B2 | 6/2004 | Weiner et al. |
| 6,760,624 B2 | 7/2004 | Anderson et al. |
| 6,760,625 B1 | 7/2004 | Kroll |
| 6,760,628 B2 | 7/2004 | Weiner et al. |
| 6,763,268 B2 | 7/2004 | MacDonald et al. |
| 6,778,856 B2 | 8/2004 | Connelly et al. |
| 6,792,316 B2 | 9/2004 | Sass |
| 6,795,730 B2 | 9/2004 | Connelly et al. |
| 6,795,736 B2 | 9/2004 | Connelly et al. |
| 6,799,069 B2 | 9/2004 | Weiner et al. |
| 6,804,557 B1 | 10/2004 | Kroll |
| 6,819,954 B2 | 11/2004 | Connelly |
| 6,819,958 B2 | 11/2004 | Weiner et al. |
| 6,829,509 B1 | 12/2004 | MacDonald et al. |
| 6,843,870 B1 | 1/2005 | Bluger |
| 6,845,266 B2 | 1/2005 | Weiner et al. |
| 6,850,805 B2 | 2/2005 | Connelly et al. |
| 6,875,180 B2 | 4/2005 | Weiner et al. |

| | | |
|---|---|---|
| 6,901,290 B2 | 5/2005 | Foster et al. |
| 6,906,256 B1 | 6/2005 | Wang |
| 6,907,295 B2 | 6/2005 | Gross et al. |
| 6,920,357 B2 | 7/2005 | Osorio et al. |
| 6,925,328 B2 | 8/2005 | Foster et al. |
| 6,944,489 B2 | 9/2005 | Zeijlemaker et al. |
| 6,949,929 B2 | 9/2005 | Gray et al. |
| 6,954,674 B2 | 10/2005 | Connelly |
| 6,961,618 B2 | 11/2005 | Osorio et al. |
| 6,985,775 B2 | 1/2006 | Reinke et al. |
| 6,993,387 B2 | 1/2006 | Connelly et al. |
| 7,006,859 B1 | 2/2006 | Osorio et al. |
| 7,010,357 B2 | 3/2006 | Helfer et al. |
| 7,013,174 B2 | 3/2006 | Connelly et al. |
| 7,015,393 B2 | 3/2006 | Weiner et al. |
| 7,047,074 B2 | 5/2006 | Connelly et al. |
| 7,054,686 B2 | 5/2006 | MacDonald |
| 7,107,097 B2 | 9/2006 | Stern et al. |
| 7,123,013 B2 | 10/2006 | Gray |
| 7,171,166 B2 | 1/2007 | Ng et al. |
| 7,174,219 B2 | 2/2007 | Wahlstrand et al. |
| 7,203,548 B2 | 4/2007 | Whitehurst et al. |
| 7,212,869 B2 | 5/2007 | Wahlstrom et al. |
| 7,221,981 B2 | 5/2007 | Gliner |
| 7,239,924 B2 | 7/2007 | Kolberg |
| 7,289,856 B1 | 10/2007 | Karicherla |
| 7,584,004 B2 | 9/2009 | Caparso et al. |
| 2002/0072782 A1 | 6/2002 | Osorio et al. |
| 2003/0083726 A1 | 5/2003 | Zeijlemaker et al. |
| 2003/0195601 A1 | 10/2003 | Hung et al. |
| 2004/0015205 A1 | 1/2004 | Whitehurst et al. |
| 2004/0147992 A1 | 7/2004 | Bluger et al. |
| 2004/0167583 A1 | 8/2004 | Knudson et al. |
| 2004/0172088 A1 | 9/2004 | Knudson et al. |
| 2004/0210291 A1 | 10/2004 | Erickson |
| 2005/0015128 A1 | 1/2005 | Rezai et al. |
| 2005/0016657 A1 | 1/2005 | Bluger |
| 2005/0107858 A1 | 5/2005 | Bluger |
| 2005/0154426 A1 | 7/2005 | Boveja et al. |
| 2005/0154435 A1 | 7/2005 | Stern et al. |
| 2005/0222642 A1 | 10/2005 | Przybyszewski et al. |
| 2005/0272280 A1 | 12/2005 | Osypka |
| 2006/0058597 A1 | 3/2006 | Machado et al. |
| 2006/0106430 A1 | 5/2006 | Fowler et al. |
| 2006/0167497 A1 | 7/2006 | Armstrong et al. |
| 2006/0173493 A1 | 8/2006 | Armstrong et al. |
| 2006/0184211 A1 | 8/2006 | Gaunt et al. |
| 2006/0224199 A1 | 10/2006 | Zeijlemaker |
| 2006/0253164 A1 | 11/2006 | Zhang et al. |
| 2006/0265025 A1 | 11/2006 | Goetz et al. |
| 2007/0027497 A1 | 2/2007 | Parnis et al. |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0060991 A1 | 3/2007 | North et al. |
| 2007/0073150 A1 | 3/2007 | Gopalsami et al. |
| 2007/0100392 A1 | 5/2007 | Maschino et al. |
| 2007/0142889 A1 | 6/2007 | Whitehurst et al. |
| 2007/0173902 A1 | 7/2007 | Maschino et al. |
| 2007/0179557 A1 | 8/2007 | Maschino et al. |
| 2007/0179579 A1 | 8/2007 | Feler et al. |
| 2007/0179584 A1 | 8/2007 | Gliner |
| 2008/0033503 A1 | 2/2008 | Fowler et al. |
| 2008/0046035 A1 | 2/2008 | Fowler et al. |
| 2008/0071323 A1 | 3/2008 | Lowry et al. |
| 2008/0200925 A1 | 8/2008 | Johnson |
| 2008/0215110 A1 | 9/2008 | Gunderson et al. |
| 2008/0255582 A1 | 10/2008 | Harris |
| 2009/0076567 A1 | 3/2009 | Fowler et al. |

FOREIGN PATENT DOCUMENTS

| | | |
|---|---|---|
| WO | 97/28668 A1 | 8/1997 |
| WO | 99/49934 A1 | 10/1999 |
| WO | 2004/069330 | 8/2004 |
| WO | 2005/114720 A2 | 12/2005 |
| WO | 2006/018447 A2 | 2/2006 |

OTHER PUBLICATIONS

Mesut Sahin, Improved Nerve Cuff Electrode Recordings with Sub-threshold Anodic Currents, IEEE Transactions on Biomedical Engineering, Aug. 1998, pp. 1044-1050, vol. 45, No. 8.

Peter J. Basser and Bradley J. Roth, New Currents in Electrical Stimulation of Excitable Tissues, Annu. Rev. Biomed. Eng. 2000, vol. 2, pp. 377-397.

PCT/US2007/016345 Search Report (Dec. 5, 2007).

MULTI-ELECTRODE ASSEMBLY FOR AN IMPLANTABLE MEDICAL DEVICE

CROSS-REFERENCE TO RELATED APPLICATIONS

This patent application is a divisional application Ser. No. 11/494,057, filed Jul. 26, 2006, published as U.S. Patent Application No. 2008/0027524, now abandoned, the contents of which is incorporated herein by reference.

BACKGROUND OF THE INVENTION

1. Field of the Invention

This invention relates generally to implantable electrode assemblies, and more particularly to an electrode assembly comprising a plurality of electrodes organized into a helical structure. The electrodes may be operatively coupled to an implantable medical device (IMD).

2. Description of the Related Art

As used herein, "stimulation" or "stimulation signal" refers to the application of an electrical, mechanical, magnetic, electro-magnetic, photonic, audio and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electro-magnetic, photonic, audio or chemical in nature) applied to the nerve in the present invention is a signal applied from an artificial source, e.g., a neurostimulator.

A "therapeutic signal" refers to a stimulation signal delivered to a patient's body with the intent of treating a disorder by providing a modulating effect to neural tissue. The effect of a stimulation signal on neuronal activity is termed "modulation"; however, for simplicity, the terms "stimulating" and "modulating", and variants thereof, are sometimes used interchangeably herein. In general, however, the delivery of an exogenous signal itself refers to "stimulation" of the neural structure, while the effects of that signal, if any, on the electrical activity of the neural structure are properly referred to as "modulation." The effect of delivery of the stimulation signal to the neural tissue may be excitatory or inhibitory and may potentiate acute and/or long-term changes in neuronal activity. For example, the "modulating" effect of the stimulation signal to the neural tissue may comprise one or more of the following effects: (a) changes in neural tissue to initiate an action potential (afferent and/or efferent action potentials); (b) inhibition of conduction of action potentials (whether endogenous or exogenously induced) or blocking the conduction of action potentials (hyperpolarizing or collision blocking), (c) affecting changes in neurotransmitter/neuromodulator release or uptake, and (d) changes in neuro-plasticity or neurogenesis of brain tissue.

Thus, electrical neurostimulation or modulation of a neural structure refers to the application of an exogenous electrical signal (as opposed to mechanical, chemical, photonic, or another mode of signal delivery) to the neural structure. Electrical neurostimulation may be provided by implanting an electrical device underneath the skin of a patient and delivering an electrical signal to a nerve such as a cranial nerve. In one embodiment, the electrical neurostimulation involves sensing or detecting a body parameter, with the electrical signal being delivered in response to the sensed body parameter. This type of stimulation is generally referred to as "active," "feedback," or "triggered" stimulation. In another embodiment, the system may operate without sensing or detecting a body parameter once the patient has been diagnosed with a medical condition that may be treated by neurostimulation. In this case, the system may periodically apply a series of electrical pulses to the nerve (e.g., a cranial nerve such as a vagus nerve) intermittently throughout the day, or over another predetermined time interval. This type of stimulation is generally referred to as "passive," "non-feedback," or "prophylactic," stimulation. The stimulation may be applied by an implantable medical device that is implanted within the patient's body. In another alternative embodiment, the signal may be generated by an external pulse generator outside the patient's body, coupled by an RF or wireless link to an implanted electrode.

Generally, neurostimulation signals that perform neuromodulation are delivered by the implantable device via one or more leads. The leads are generally coupled at a distal end to electrodes, which are coupled to a tissue in the patient's body. Multiple leads/electrodes may be attached to various points of a nerve or other tissue inside a human body for delivery of neurostimulation. Generally, each lead is associated with a separate electrode, particularly when each of the electrodes is intended to perform a different function (e.g., deliver a first electrical signal, deliver a second electrical signal, sense a body parameter, etc.).

Generally, a single electrode is associated with each lead originating from the IMD. The number of leads that originate from the IMD is limited due to the size constraints of the IMD and of the patient's body. Therefore, a limited number of electrodes using state-of-the-art technology can be used to deliver electrical stimulation from an IMD.

Further, state-of-the-art medical systems call for performing a stimulation during a time period that is separate from a time period of performing a sensing function for sensing the patient's biological signals. Further, a first lead associated with a first electrode may deliver a therapeutic electrical signal, while a second lead associated with a second electrode may perform data acquisition for sensing of various biometric parameters in the patient's body. This process may be inefficient since the state-of-the-art generally lacks a system for simultaneously delivering an electrical signal to a neural structure and sensing electrical activity, particularly where associated with the neural structure to which the signal is applied. Further, problems with the state-of-the-art also include a limitation on the number of electrodes that may be employed by an IMD to deliver various stages of therapy and/or sensing functions.

SUMMARY OF THE INVENTION

In one aspect, the present invention provides an electrode assembly comprising a plurality of electrodes for use with an implantable medical device for conducting an electrical signal between the implantable medical device and a target tissue. The electrode assembly includes a helical member having a first and a second electrode formed upon the helical member. The first and second electrodes are adapted to deliver the electrical signal. The electrode assembly also includes a first conductive element formed upon the helical member and operatively coupled to the first electrode. The first conductive element is adapted to carry the electrical signal to the first electrode. The electrode assembly also includes a second conductive element formed upon the helical member and operatively coupled to the second electrode.

In yet another aspect, the present invention includes a method for forming a helical electrode assembly for carrying an electrical signal associated with an implantable medical device. A first layer is formed on a generally flat substrate. In one embodiment, the substrate is generally planar. A first conducting structure is formed upon the first layer. The first conducting structure includes a first electrode and a first lead operatively coupled to the first electrode. A second, non-conductive layer is formed above the first layer. A second conducting structure is formed upon the second, non-conductive layer. The second conducting structure includes a second electrode and a second lead operatively coupled to the second electrode. The method further includes the step of forming the generally flat substrate into a helical structure.

In another aspect, the present invention includes another method for forming a helical electrode assembly for carrying a signal associated with an implantable medical device. A first layer is formed on a generally flat substrate. A first conducting structure and a second conducting structure are formed upon the first layer. The first conducting structure includes a first electrode and a first lead operatively coupled to the first electrode. The second conducting structure includes a second electrode and a second lead operatively coupled to the second electrode. A second, non-conductive layer is formed such that the first and second leads are substantially covered by the second layer and the first and second electrodes remain exposed. The method also comprises the step of forming the generally flat substrate and first and second layers into a helical structure.

In yet another aspect, the present invention provides an implantable medical system for providing a therapeutic electrical signal to a target tissue using a helical electrode assembly. The system of the present invention includes an implantable medical device for generating a therapeutic electrical signal. The system also includes a lead assembly operatively coupled to the implantable medical device and adapted to carry the therapeutic electrical signal. The lead assembly comprises first and second lead elements. The system also includes an electrode assembly operatively coupled to the lead assembly. The electrode assembly includes a helical member having first and second electrodes formed thereon. The electrode assembly also includes a first conductive element formed upon the helical member and operatively coupled to the first electrode and to the first lead element. The electrode assembly also includes a second conductive element formed upon the helical member and operatively coupled to the second electrode and to the second lead element. The first and second electrodes are adapted to deliver the electrical signal to tissue of a patient when coupled thereto.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Certain terms are used throughout the following description and claims to refer to particular system components. This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium therebetween. The presence of substances, such as bodily fluids, that do not substantially attenuate electrical connections does not vitiate direct contact. The word "or" is used in the inclusive sense (i.e., "and/or") unless a specific use to the contrary is explicitly stated.

As used herein, "stimulation" or "stimulation signal" refers to the application of an electrical, mechanical, and/or chemical signal to a neural structure in the patient's body. In one embodiment, the stimulation comprises an electrical signal. The stimulation signal may induce afferent and/or efferent action potentials on the nerve, may block native afferent and/or efferent action potentials, or may be applied at a sub-threshold level that neither generates action potentials nor blocks native action potentials.

The stimulation signal applied to the neural structure in embodiments of the present invention refers to an exogenous signal that is distinct from the endogenous electrical, mechanical, and chemical activity (e.g., afferent and/or efferent electrical action potentials) generated by the patient's body and environment. In other words, the stimulation signal (whether electrical, mechanical or chemical in nature) applied to the nerve in the present invention is from an artificial source, e.g., a neurostimulator.

The term "electrode" or "electrodes" described herein may refer to one or more stimulation electrodes, one or more sensing electrodes, and/or to one or more electrodes that are capable of delivering a stimulation signal as well as performing a sensing function. Stimulation electrodes may refer to an electrode that is capable of delivering a stimulation signal to a tissue of a patient's body. A sensing electrode may refer to an electrode that is capable of sensing a physiological indication of a patient's body. "Electrode" and/or "electrodes" may also refer to one or more electrodes capable of delivering a stimulation signal as well as sensing a physiological indication.

The terms "stimulating" and "stimulator" may generally refer to delivery of a stimulation signal to a neural structure. The effect of such stimulation on neuronal activity is termed "modulation"; however, for simplicity, the terms "stimulating" and "modulating", and variants thereof, are sometimes used interchangeably herein. In general, however, the delivery of an exogenous signal refers to "stimulation" of the neural structure, while the effects of that signal, if any, on the electrical activity of the neural structure are properly referred to as "modulation." In one embodiment of the present invention, methods, apparatus, and systems are provided involving a helical electrode to stimulate an autonomic nerve, such as a cranial nerve, e.g., a vagus nerve, using an electrical signal to treat a medical condition such as epilepsy and other movement disorders, mood and other neuropsychiatric disorders, dementia, coma, migraine headache, obesity, eating disorders, sleep disorders, cardiac disorders (such as congestive heart failure and atrial fibrillation), hypertension, endocrine disorders (such as diabetes and hypoglycemia), and pain, among others. A generally suitable form of neurostimulator for use in the method and apparatus of the present invention is disclosed, for example, in U.S. Pat. No. 5,154,172, assigned to the same assignee as the present application. The neurostimulator may be referred to a NeuroCybernetic Prosthesis (NCP®, Cyberonics, Inc., Houston, Tex., the assignee of the present application). Certain parameters of the electrical stimulus generated by the neurostimulator are programmable, such as by means of an external programmer in a manner conventional for implantable electrical medical devices.

Embodiments of the present invention provide for an electrode assembly comprising a plurality of individual electrodes or an array of electrodes. The electrode assembly may be formed as a helical structure, wherein the electrode assembly may comprise a plurality of electrodes and associated conductive elements for delivering various electrical stimulation signals. One or more of the plurality of electrodes associated with the electrode assembly may also provide for the capacity to perform sensing. Therefore, substantially simultaneous delivery of stimulation and the acquisition of sensing signals may be performed utilizing the electrode array of the electrode assembly of the present invention. The term "electrode array" may refer to two or more electrodes residing on a single electrode assembly.

Embodiments of the present invention provide a flexible "ribbon-type" material upon which various electrodes may be provided in a variety of configurations to provide efficient delivery of therapy and/or sensing functions. For example, electrodes may be positioned on a helical member such that successive electrodes are generally linear along an axis of a nerve, such as the vagus nerve. Alternatively, various electrodes on the electrode assembly of the present invention may be positioned in a staggered fashion to deliver a signal in a particular geometry or configuration to target portions of a nerve. An electrode assembly may be employed using a state-of-the-art IMD such that a number of electrodes may be substantially simultaneously activated, or alternatively, activated in a staggered or sequential fashion.

Embodiments of the present invention also provide for a method for manufacturing an electrode assembly that comprises a plurality of electrodes. A non-conductive material may be coated with various layers of conductive and non-conductive films or layers to create various conductive structures, such as electrodes, strips of conductive materials that provide electrical signals to the electrodes, and interfaces that provide connection between the various electrodes on the electrode assembly and lead(s) that are in operative communication with the IMD. For example, photolithography processes may be used on a plurality of layers formed on a substrate to provide various electrodes that are situated at desirable or strategic locations on a single electrode assembly, which may be formed into a helical configuration. This helical configuration may be used to wrap the electrode assembly around various portions of a patient's body, such as a nerve, such that the multiple electrodes may come into contact at desired locations of a particular nerve in a desired geometry or configuration. One or more of the multiple electrodes may be energized in a strategically timed fashion to provide desired stimulation to a portion of a patient's body. This may provide the ability to direct or steer current flow to a pre-determined position and direction, through a portion of a patient's body, such as a nerve. Utilizing embodiments of the present invention more efficient and effective delivery of stimulation may be realized.

Figure 1:
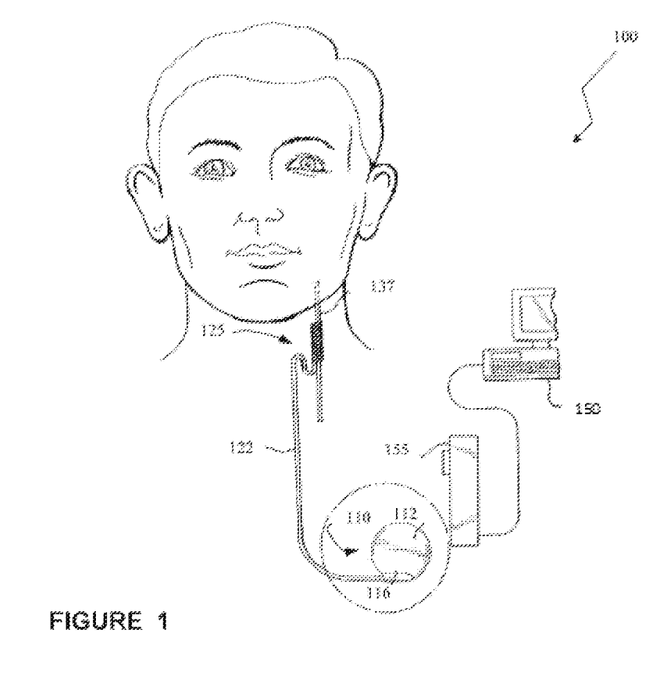
FIG. 1 is a stylized diagram of an implantable medical device implanted into a patient's body for providing stimulation to a portion of the patient's body, in accordance with one illustrative embodiment of the present invention.

Although not so limited, a system capable of implementing embodiments of the present invention is described below. FIG. 1 depicts a stylized implantable medical system 100 for implementing one or more embodiments of the present invention. FIG. 1 illustrates an electrical signal generator 110 having main body comprising a case or shell 112 with a header 116 for connecting to leads 122. The generator 110 is implanted in the patient's chest in a pocket or cavity formed by the implanting surgeon just below the skin, similar to the implantation procedure for a pacemaker pulse generator.

A nerve electrode assembly 125, preferably comprising a plurality of electrodes, is conductively connected to the distal end of an insulated, electrically conductive lead assembly 122, which preferably comprises a plurality of lead wires (one wire for each electrode). Each electrode in the electrode assembly 125 may operate independently or alternatively, may operate in conjunction with each other to form a cathode and an anode. The electrode assembly 125 illustrated in FIG. 1 may be formed into a helical structure that comprises a plurality of electrodes on an inside surface of the helical structure to deliver electrical signals via the plurality of electrodes in a simultaneous or time-delayed fashion, as well as perform efficient sensing of electrical signals in a patient's body.

Lead assembly 122 is attached at its proximal end to connectors on the header 116 on the case 112. The electrode assembly 125 at the distal end of lead assembly 122 may be surgically coupled to a target tissue such as vagus nerve 137. The electrical signal may also be applied to other cranial nerves. The electrode assembly 125 preferably comprises a bipolar stimulating electrode pair, or may comprise three, four or even more electrodes. The electrode assembly 125 is preferably wrapped around the target tissue, such as a vagus nerve. Prior art electrodes have been provided that wrap around a target tissue, such as the electrode pair described in U.S. Pat. No. 4,573,481. In the prior art structures, however, a separate helical element is provided for each electrode. In contrast, the present invention involves a plurality of electrodes on a single helical element. Varying lengths of the helical element may be provided, depending upon the pitch of the helix and the number of electrodes thereon. Lengths may range from 3 mm to 50 mm, although even smaller or longer helices may be employed in particular applications. Lead assembly 122 may be secured, while retaining the ability to flex with movement of the chest and neck, by a suture connection to nearby tissue.

In one embodiment, the open helical design of the electrode assembly 125 is self-sizing and flexible, minimizes mechanical trauma and allows body fluid interchange with the target tissue. The electrode assembly 125 preferably conforms to the shape of the target tissue, providing a low stimulation threshold by allowing a large stimulation contact area. Structurally, the electrode assembly 125 comprises a plurality of electrode ribbons (not shown), of a conductive material such as precious metals and/or alloys and oxides thereof, including platinum, iridium, platinum-iridium alloys, and/or oxides of the foregoing. The electrode ribbons are individually bonded to an inside surface of an elastomeric body portion, which may comprise a helical assembly. The lead assembly 122 may comprise two distinct lead wires or a multi-wire cable whose conductive elements are respectively coupled to one of the conductive electrode ribbons. The elastomeric body portion is preferably composed of silicone rubber, or another biocompatible, durable polymer such as siloxane polymers, polydimethylsiloxanes, polyurethane, polyether urethane, polyetherurethane urea, polyesterurethane, polyamide, polycarbonate, polyester, polypropylene, polyethylene, polystyrene, polyvinyl chloride, polytetrafluoroethylene, polysulfone, cellulose acetate, polymethylmethacrylate, polyethylene, and polyvinylacetate.

The electrical signal generator 110 may be programmed with an external computer 150 using programming software of the type copyrighted by the assignee of the instant application with the Register of Copyrights, Library of Congress, or other suitable software based on the description herein, and a programming wand 155 to facilitate radio frequency (RF) communication between the computer 150 and the signal generator 110. The wand 155 and software permit non-invasive communication with the generator 110 after the latter is implanted, according to means known in the art.

A variety of stimulation therapies may be provided in implantable medical systems 100 of the present invention. Different types of nerve fibers (e.g., A, B, and C fibers being different fibers targeted for stimulation) have different conduction velocities and stimulation thresholds and, therefore, differ in their responsiveness to stimulation. Certain pulses of an electrical stimulation signal, for example, may be below the stimulation threshold for a particular fiber and, therefore, may generate no action potential in the fiber. Thus, smaller or narrower pulses may be used to avoid stimulation of certain nerve fibers (such as C fibers) and target other nerve fibers (such as A and/or B fibers, which generally have lower stimulation thresholds and higher conduction velocities than C fibers). Additionally, techniques such as pre-polarization may be employed wherein particular nerve regions may be polarized before a more robust stimulation is delivered, which may better accommodate particular electrode materials. Furthermore, opposing polarity phases separated by a zero current phase may be used to excite particular axons or postpone nerve fatigue during long term stimulation.

Figure 2:
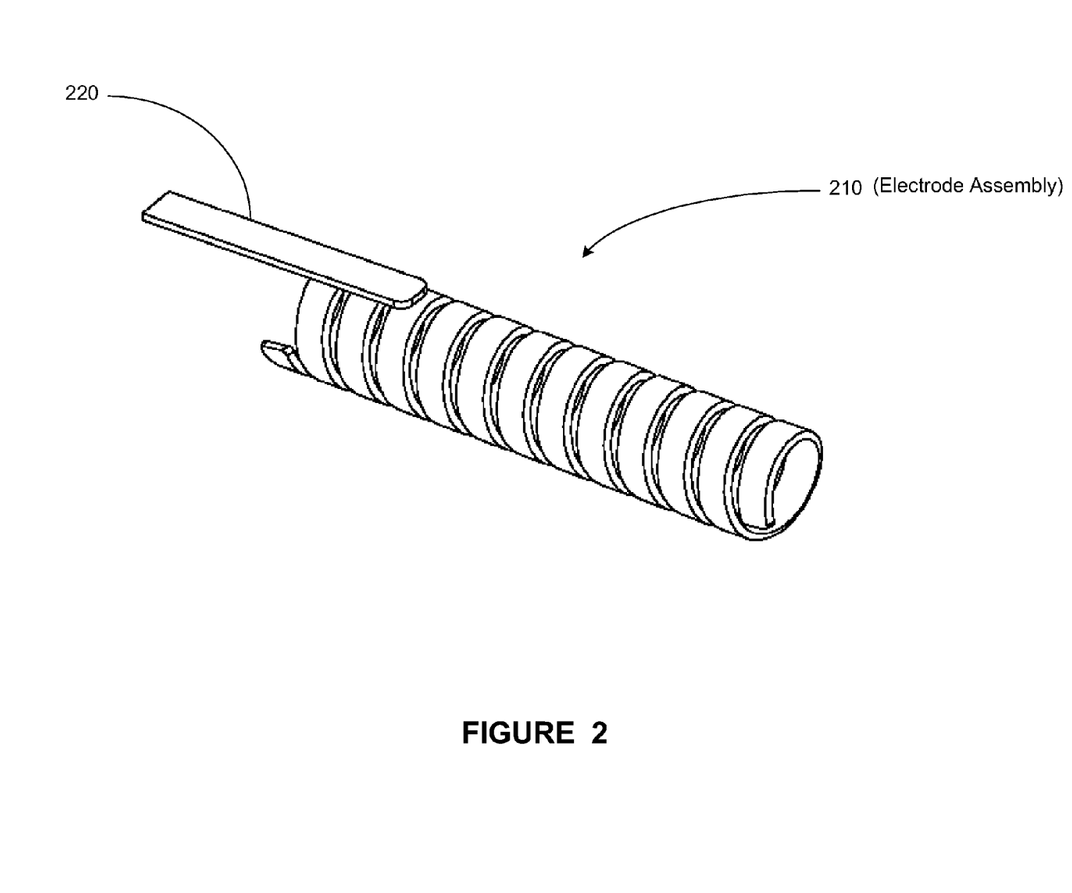
FIG. 2 illustrates a stylized isometric illustration of an electrode assembly in accordance with one embodiment of the present invention.

Turning now to FIG. 2, a stylized isometric illustration of a helical electrode assembly 210 in accordance with one embodiment of the present invention is illustrated. The electrode assembly may be formed into a helical configuration and may be made of a flexible material, such as a silicone polymer substrate with semiconductor layers imprinted thereon using photolithography techniques. The electrode assembly may also comprise an end member 220 that provides an interface to a lead wire in electrical communication with the IMD. The helical structure of FIG. 2 may be wrapped around a portion of the patient's body, such as a nerve, e.g., the vagus nerve, and anchored thereupon.

Figure 3:
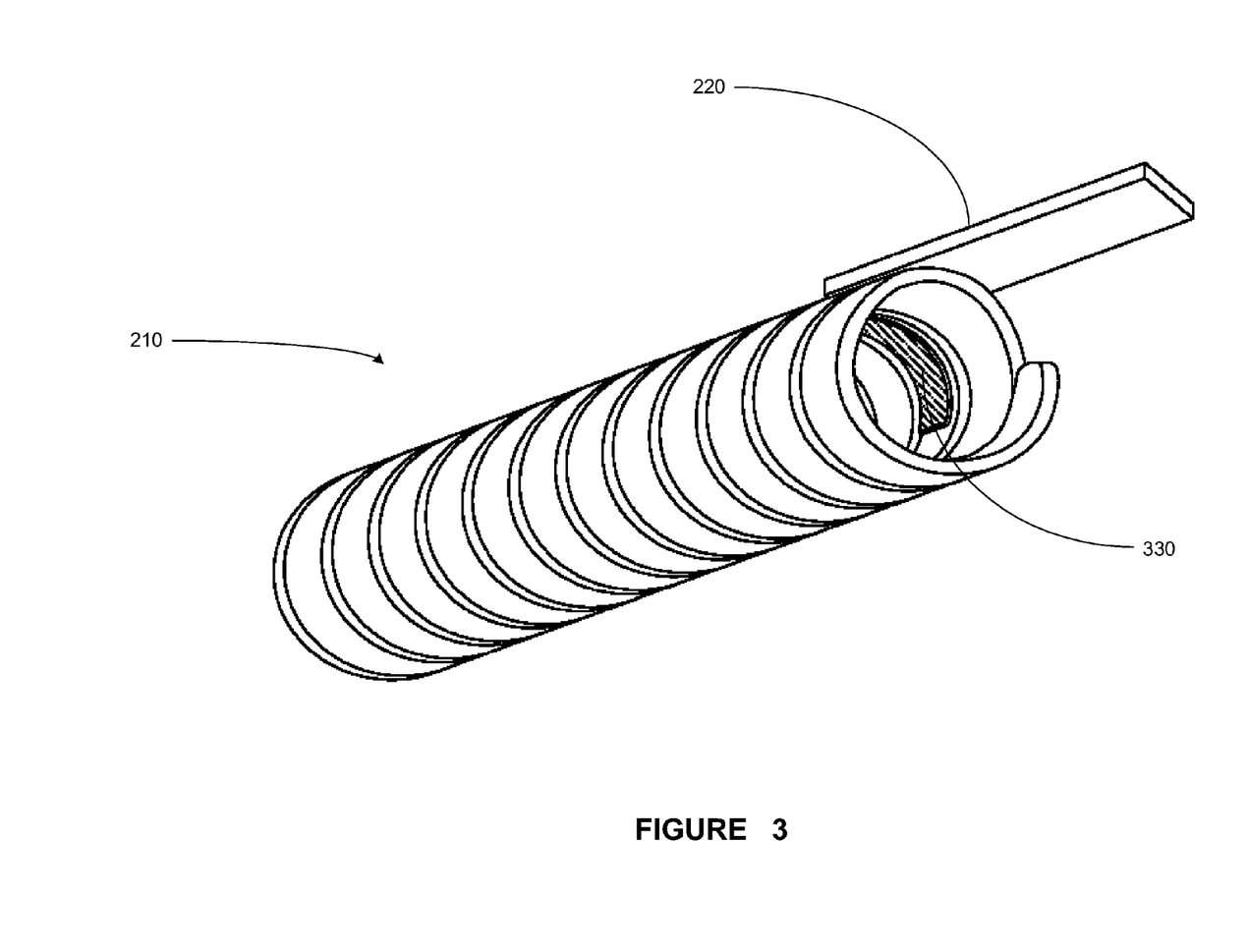
FIG. 3 illustrates another isometric depiction of the electrode assembly and an electrode in accordance with one illustrative embodiment of the present invention.

Turning now to FIG. 3, another isometric depiction of the electrode assembly 210, in accordance with one illustrative embodiment of the present invention, is provided. An electrode 330 may be formed on the surface of the inside portion of the electrode assembly 210. The electrode assembly 210 may be wrapped around a target portion of the patient's body, e.g., a nerve, such that the electrode 330 contacts the target portion at a predetermined location. The electrode 330 illustrated in FIG. 3 may comprise a plurality of electrodes formed on the inside surface of various portions of the electrode assembly 210. The electrodes 330 may comprise a conductive material such as platinum, iridium, and/or platinum/iridium alloys and/or oxides. Further details as to the position of the electrodes on the electrode assembly 210 are provided in subsequent drawings and accompanying description below.

Figure 4:
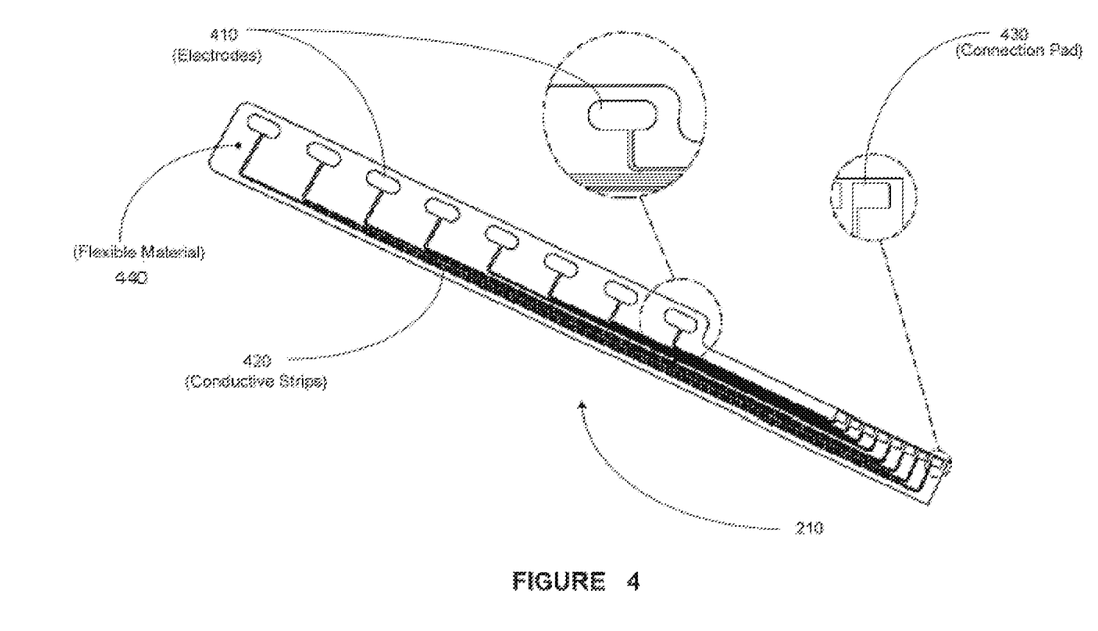
FIG. 4 illustrates a stylized depiction of the electrode assembly of FIGS. 2 and 3 during fabrication, in accordance with the illustrated embodiment of the present invention.

Turning now to FIG. 4, a stylized depiction is provided of the electrode assembly 210 during fabrication in accordance with an embodiment of the present invention. The electrode assembly 210 comprises a flexible substrate material 440 on which various electrodes may be formed. Flexible substrate materials 440 upon which a plurality of electrodes may be formed may comprise various materials, such as silicone rubbers, siloxane polymers, and other materials previously noted.

Various conductive structures in a variety of manners may be formed upon the flexible material 440. The conductive structures may include one or more electrodes 410, which are capable of being in contact with a portion of a patient's body, e.g., a nerve, and provide an electrical signal from the signal generator 110 or detect electrical signals in the patient's body. The conductive structures may also include various conductive strips 420 and a plurality of connection pads 430. Each of the electrodes 410 may be respectively coupled electrically to a distal end of one of a plurality of conductive strips 420 that are capable of carrying electrical signals to or from the electrodes 410. Further, each of the conductive strips 420 may be respectively coupled electrically, at a proximal end thereof, to one of the plurality of connection pads 430. The connection pads 430 may then be used as an interface to a wire or a lead structure that may contain several electrical components that may each respectively attach or connect to the set of connection pads 430 illustrated in FIG. 4.

Connection pads 430 may be formed at the edge of the helical structure or on the end portion 220 of FIG. 2. In one embodiment, the end portion 220 may be part of the flexible material 440 (as depicted in FIG. 4), upon which various processes described herein may be used to form the connection pads 430. In an alternative embodiment, the end portion 220 may be a separate structure that is coupled to the helical structure, as indicated in FIGS. 2 and 3. The end portion may house a plurality of connection pads 430. Continuing referring to FIG. 4, in one embodiment, the portion of the flexible material 440 that contains the electrodes 410 may be shaped into a helical form, while the portion of the flexible material 440 that comprises the conductive strips 420 may be shaped into an undulated form, and the portion of the flexible material 440 that comprises the connection pads 430 may be formed in a generally flat configuration. In this manner, a connector (not shown in FIG. 4) may be coupled to the connection pads 430, wherein a lead assembly that comprises a plurality of electrical wires may be operatively coupled to connection pads 430. Therefore, electrical connections between a plurality of electrical wires in a lead assembly may be respectively operatively coupled to a plurality of electrodes 410.

Various methods may be used to form the conductive elements illustrated in FIG. 4 upon the flexible material 440 in a flat or generally planar initial configuration. Semiconductor processing techniques, such as photolithography processes, copper deposition processes, single and/or dual damascene processes, etc., known to those skilled in the art having benefit of the present disclosure, may be employed to form the conductive structures (e.g., 410, 420, 430) upon the flexible material 440. The flexible material 440 may then be formed into a helical structure, wherein the electrodes 410 are located on an inner surface of the helical structure such that the electrodes would be in electrical communication with a patient's body when the electrode assembly 210 is wrapped around a target structure.

In one embodiment, the flexible material 440 is formed into a helical structure after creating conductive structures 410, 420, 430, e.g., on the material 440 while the material 440 is in a flat or generally planar configuration. The flat substrate material 440 is then formed into a helical configuration. In an alternative embodiment, the flexible material 440 is first formed into a helical structure, which is then unfurled into a flat or generally planar configuration. The conductive structures are then created on the unfurled, flat material, and thereafter a restraining force on the unfurled structure is released to allow it to return to a helical configuration. Further, a portion of the flexible material 440 may be shaped in an undulated form. In one embodiment, a portion of the flexible material 440 that comprises conductive structures may be shaped into an undulated form. Known fabrication techniques may be used to form the flexible material into a helical structure and/or into an undulated structure, such as heat treating and/or annealing techniques, and scoring and/or etching portions of the substrate to urge the substrate into a helical configuration.

Figure 5:
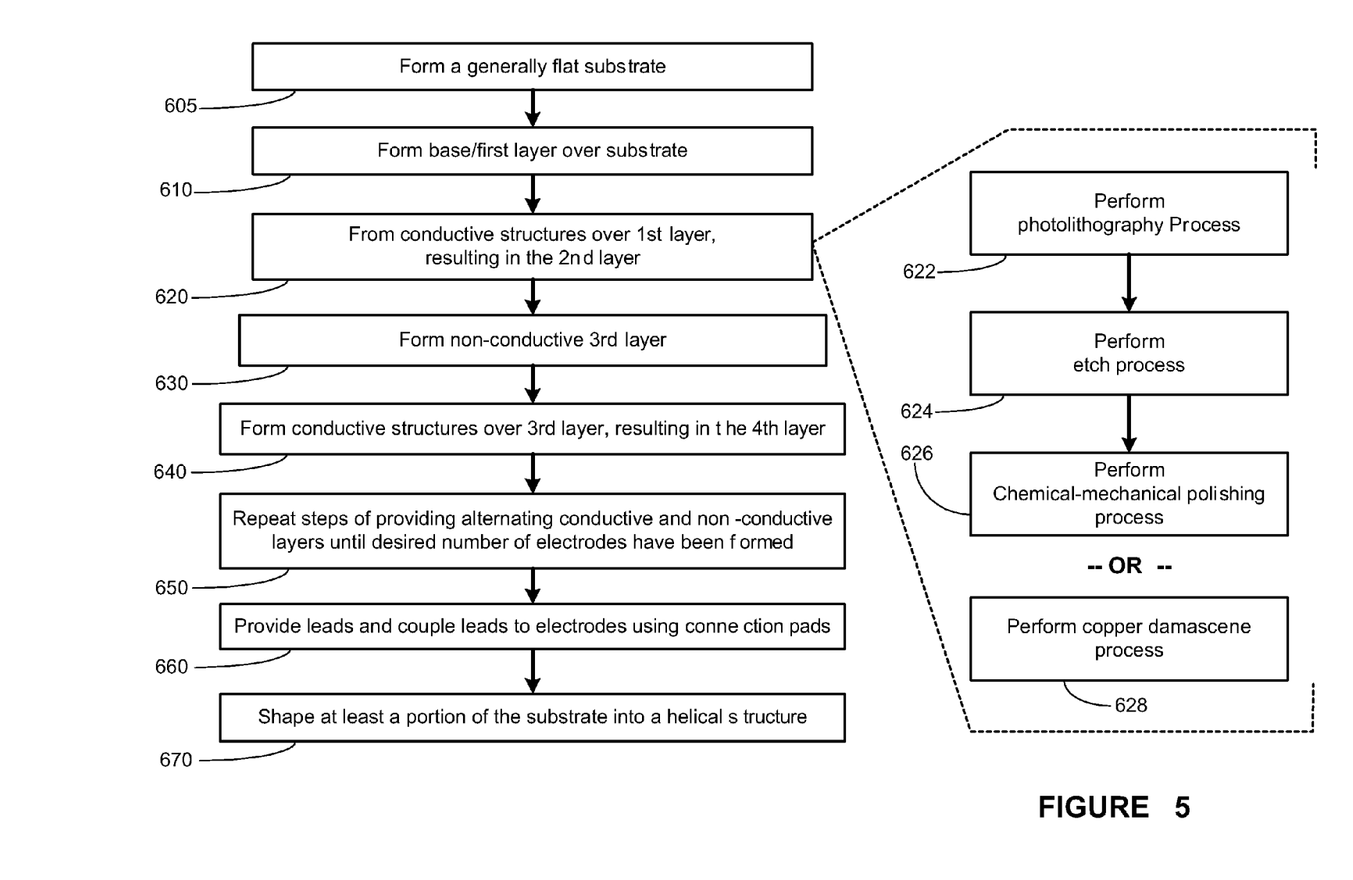
FIG. 5 illustrates a flowchart associated with a method for providing the electrode assembly of FIGS. 2-4, in accordance with an illustrative embodiment of the present invention, is provided.

Turning now to FIG. 5, a flowchart associated with a method for providing the electrode assembly 210 in accordance with an illustrative embodiment of the present invention, is provided. Initially, a substrate is provided comprising a flexible material (block 605). In one embodiment, the substrate is generally flat. In another embodiment, the substrate is generally planar. A base layer or first layer may be formed on the substrate that is part of the flexible material 440 of FIG. 4 (block 610). Numerous types of deposition techniques known to those skilled in the art having benefit of the present disclosure may be used to generate the base layer. Such techniques may include, without limitation, chemical plating, plasma ion deposition, vapor deposition and sputtering. In one embodiment, the base layer is a substantially non-conductive film of material, such as a dielectric material.

A conductive structure may then be formed over the first layer to form a second layer (block 620). The conductive structure may include the electrode 410, the conductive strip 420, the connection pads 430, etc. Various techniques may be used to form the conductive structures on the second layer. The formation of the conductive structure may include various semiconductor processing steps, such as performing a photolithography process (block 622). The photolithography process may use a mask and a light source to provide for deposition of material in a predetermined desired formation to form one or more electrodes 410, conductive strips 420, and/or connection pads 430. An etch process may also be performed on the second layer (block 624). The etch process may be used to etch away excessive deposition material in order to conform the various conductive structures into predetermined shapes and sizes. In one embodiment, an excimer laser may be used to remove excessive deposition material, e.g., removing excessive polymer deposition material to expose a precisely defined surface area for an electrode 410. For example, the dimensions of the electrode may be precisely controlled to provide a width of from about 0.1 mm to about 2.0 mm, with a typical width of about 1.0 mm, and a length of from about 0.1 mm to about 10 mm, typically about 7 mm. The widths of the conductive strips may range from about 20 µm to about 100 µm (0.1 mm), with lengths thereof varying as necessary for a particular application. The connection pads may be provided with dimensions sufficient to allow good electrical connection to a lead wire, which will vary according the application. In one embodiment, the connection pads may be provided with major dimensions ranging from about 20 µm to about 3 mm. Further, a chemical-mechanical polishing (CMP) process may also be performed on the second layer (block 626). Various semiconductor processing techniques may be performed to form the conductive structures over the first layer. Alternatively, a copper deposition process, such as a damascene process or a dual damascene process, may be performed to form the conductive structures of the second layer (block 628).

Upon forming one or more conductive structures over the first layer to form the second layer, a non-conductive layer may then be formed over the second layer, resulting in a third layer (block 630). Another set of conductive structures may then be formed over the third layer to form the fourth layer that contains additional conductive structures (block 640). This set of processes (i.e., forming alternating non-conducting and conducting layers) may then be repeated until a desired number of electrodes, as well as associated conductive strips and connection pads, are formed on the flexible material 440 (block 650). Additionally, upon completion of the formation of the conductive portions on the flexible material, additional coating steps may be performed. The coating steps may include coating the electrode assembly with a non-conductive, flexible coating while masking off the electrodes. Optionally, a lead assembly having a plurality of lead elements may be provided, and the lead elements may be coupled to the electrodes using the connection pads (block 660). In this manner, an electrode assembly 210 with a helical electrode portion comprising a plurality of electrodes, conductive strips, and connection pads is provided. The electrode assembly may be coupled to a lead assembly, which may have an undulated form, using the connection pads. At least a portion of the substrate may be formed into a helical shape (block 670). In one embodiment, the portion of the substrate containing the electrodes may be formed into a helical shape.

Figure 6:
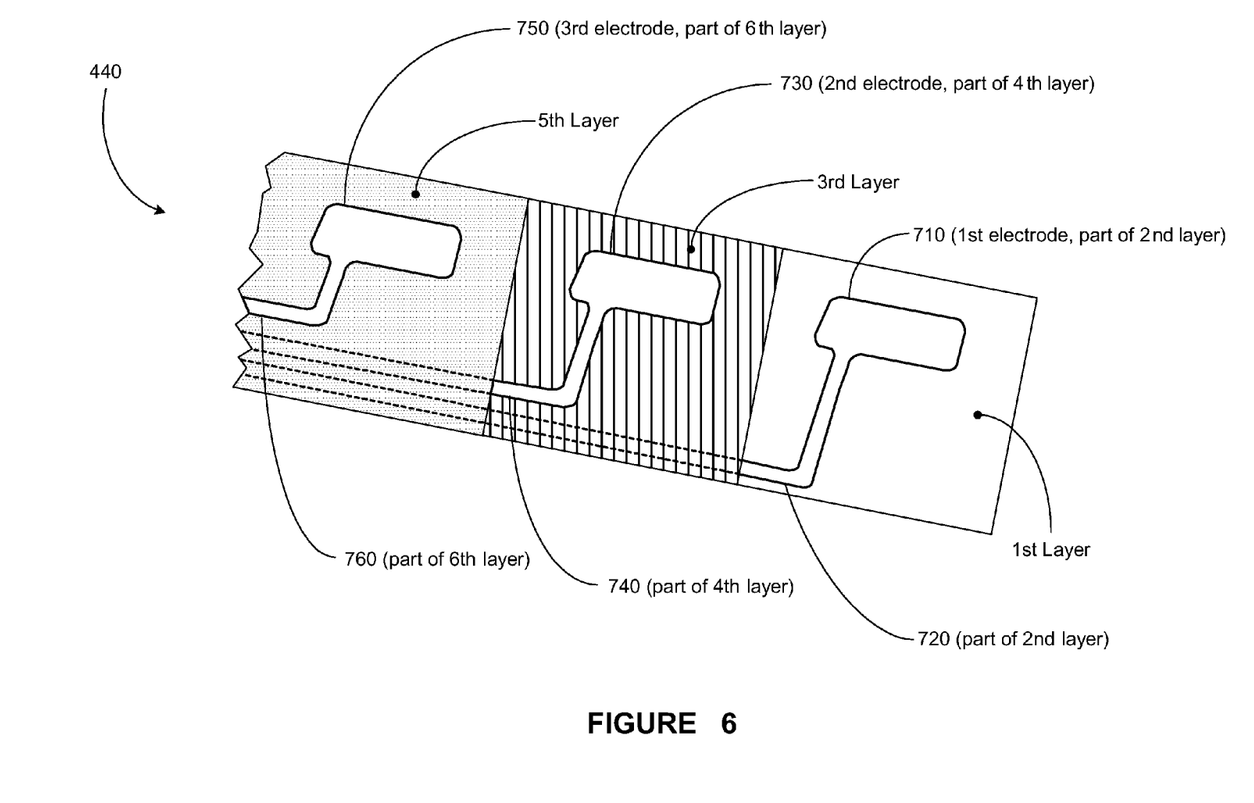
FIG. 6 illustrates a stylized depiction of the electrode assembly of the present invention in a staggered multi-layered configuration, in accordance with an illustrative embodiment of the present invention.

Turning now to FIG. 6, a stylized depiction of the electrode assembly of the present invention in a staggered, multi-layered configuration is provided in accordance with an illustrative embodiment of the present invention. The flexible material 440 may comprise a first layer upon which a first electrode 710 and an associated conductive strip 720 are formed into a second layer using the various techniques described above. The conductive strip runs along at least a portion of the length of the flexible material 440 and is illustrated as dotted lines under subsequent layers that are formed on the connector strip (i.e., flexible material) 440, such as a third layer, and a fourth layer.

Upon forming of the first layer and the second layer (which includes the first electrode 710 at a predetermined location, and associated conductive strip 720 that runs along the length of the flexible material 440), a third layer is formed. The third layer is formed at an offset position on the second layer such that the third layer is not formed above the region in which the first electrode 710 resides. Upon the third layer, a fourth layer comprising a second electrode 730 and an associated second conductive strip 740 may be formed. The second conductive strip 740 may run along a portion of the length of the flexible material 440.

Further, offset slightly from the third and fourth layers, a fifth layer may be formed over the fourth layer. The fifth layer is not formed above the portion of the first and second or third and fourth layers upon which the first electrode 710 or the second electrode 730 reside. Upon the fifth layer, a sixth layer comprising a third electrode 750 and an associated third conductive strip 760 are formed. The third conductive strip 760 runs along a portion of the length of the flexible material 440. In this manner, a "stair step" of layers that contain electrodes and conductive strips are generated on a single flexible material 440 until a desired number of electrodes are formed. Further, each layer upon which an electrode is formed may also contain a respective connection pad for coupling the electrode and its associated conductive strip to a lead element. Due to the offsetting of the third and fifth layers, both the conductive strips and the electrodes (in other words, the entire conducting structures) are offset from one another, such that all the electrodes are exposed on the surface of the electrode assembly. In addition, the surface of the electrode assembly is designed so that an electrode is exposed only where it comes into contact with a portion of the patient's body.

Upon forming the flexible material 440 into a helical structure, and subsequently wrapping the helical structure around a portion of the patient's body, such as a nerve, each of the first through third electrodes 710, 730, 750, comes into contact with respective portions of the patient's body without contacting the other electrodes or the conductive strips 720, 740, 760 associated with the other electrodes. That is, each individual electrode is electrically isolated from the other electrodes and from the conductive strips associated with the other electrodes. Thus, different electrical signals can be applied to different regions of the patient's body, independently. Further, the first electrode 710 may deliver a therapeutic stimulation signal, whereas the second electrode 730 may acquire resultant electrical data, e.g., by sensing the activity on the nerve. In this manner, the IMD is capable of independently controlling the electrical activities of each of the electrodes.

Figure 7:
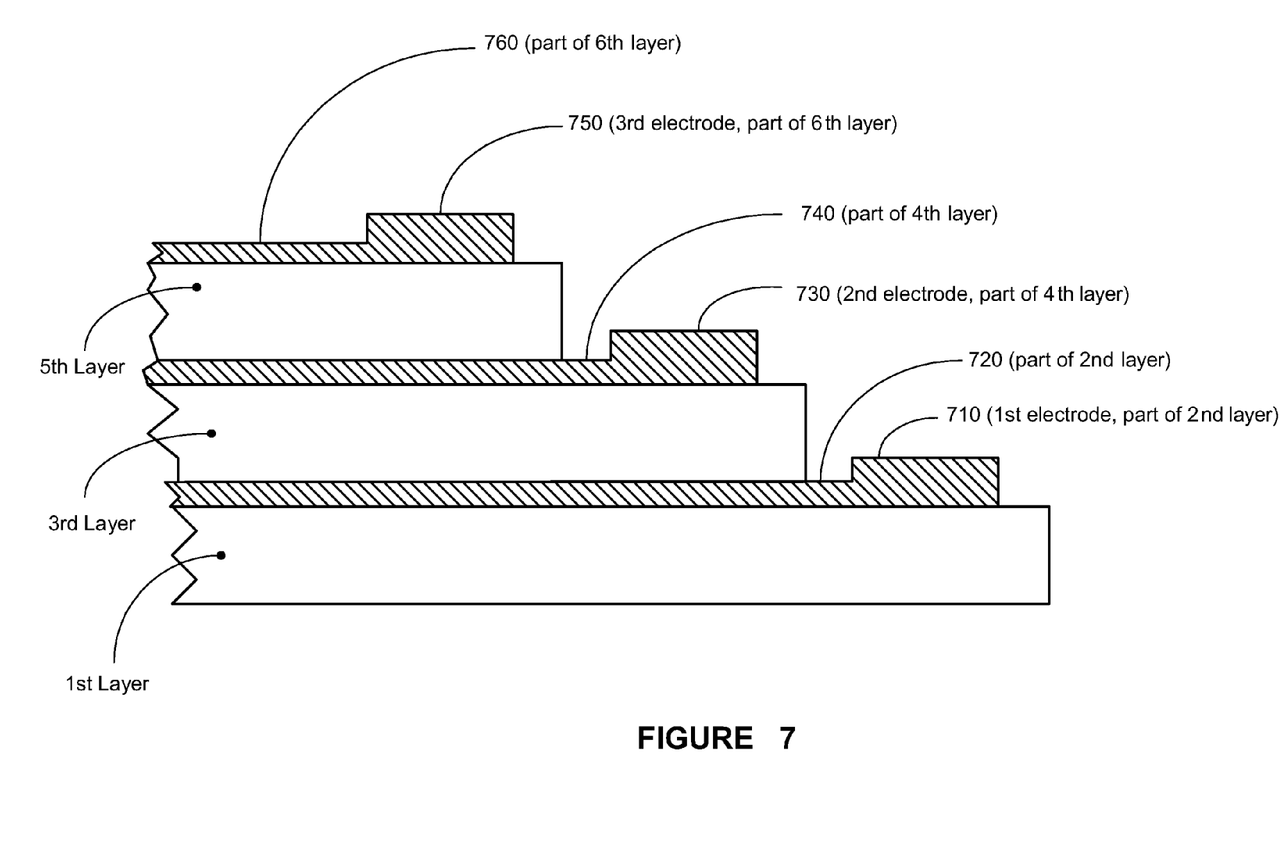
FIG. 7 illustrates a stylized side view of a flexible material upon which a first through third layers and corresponding conductive structures are formed, in accordance with an illustrative embodiment of the present invention.
Figure 8:
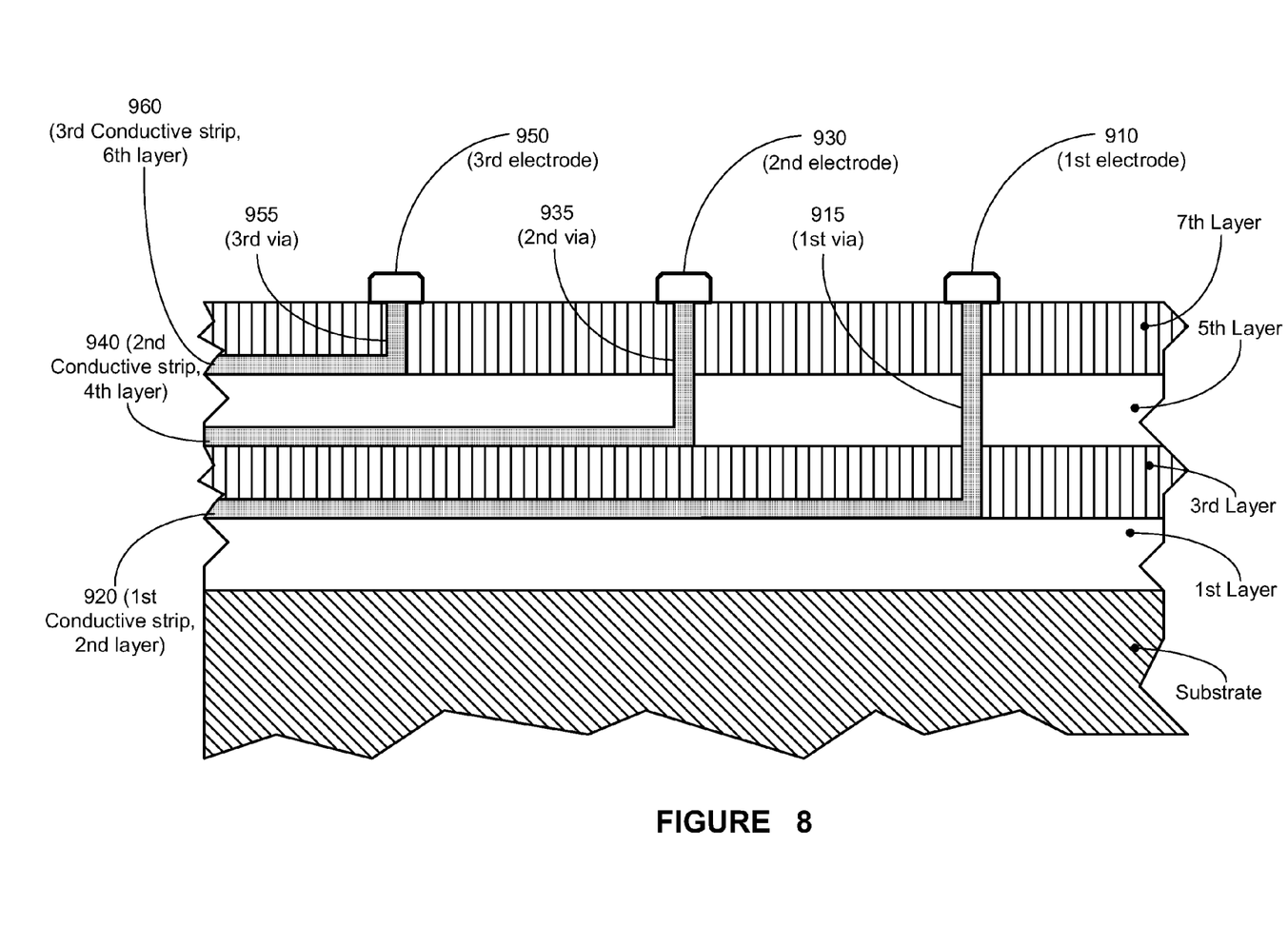
FIG. 8 illustrates an alternative stylized depiction of the electrode assembly of the present invention in a multi-layered configuration, in accordance with an illustrative embodiment of the present invention.

Referring simultaneously to FIGS. 7 and 8, a stylized side view of the flexible material 440 upon which the first through sixth layers are formed, is illustrated in FIG. 7. FIG. 8 illustrates the first through seventh layers that are formed above the substrate on the flexible material 440. As depicted in FIG. 7, a first layer is formed above the substrate (substrate not shown in FIG. 7). Above the first layer, the second layer comprising the first electrode 710 and the first conductive strip 720 are formed. Without being formed above the first electrode 710, the third layer is formed, at an offset position on the second layer. The fourth layer, comprising the second electrode 730 and the second conductor strip 740, is formed upon the third layer. The third layer is capable of electrically isolating the conductive structures in the second layer. Similarly, upon forming the conductive structures into a fourth layer above the third layer, the fifth layer is formed at an offset position on the fourth layer, above a portion of the conductive strip portion of the fourth layer and without being formed above the second electrode 730. Upon the fifth layer, a sixth layer comprising the third electrode 750 and the associated third conductive strip 760 are formed. Therefore, the thickness of the overall electrode assembly 210 will depend on the number of electrodes that are formed on the flexible material 440. Due to the offsetting of the third and fifth layers, both the conductive strips and the electrodes (in other words, the entire conducting structures) are offset from one another, such that all the electrodes are exposed on the surface of the electrode assembly. In addition, the surface of the electrode assembly is designed so that an electrode is exposed only where it comes into contact with a portion of the patient's body, such that each individual electrode is electrically isolated from the other electrodes and from the conductive strips associated with the other electrodes. In this manner, each of the first through third electrodes 710, 730, 750, or additional electrodes that may be formed on the flexible material 440, may operate independently. Although only six layers and three electrodes are illustrated for clarity and ease of description, those skilled in the art having benefit of the present invention would readily appreciate that various additional layers may be similarly added and remain within the spirit and scope of the present invention.

Referring to FIG. 8, an alternative embodiment of providing the electrode assembly in accordance with an alternative illustrative embodiment of the present invention, is provided. FIG. 8 illustrates a substrate associated with the flexible material 440. Upon the substrate, a first layer may be formed. Upon the first layer, a second layer comprising a first conductive strip 920 is formed. The second layer is formed at an offset position on the first layer. The first conductive strip 920 may be connected to a corresponding electrode that will be formed upon another layer.

Subsequently, a third layer is formed above the first and second layers. The third layer is formed upon the first layer as well as the first conductive strip 920 which comprises the second layer. A channel may be grooved into the third layer to provide for the formation of a first via 915. A fourth layer comprising a second conductive strip 940 is formed above the third layer to be connected to a corresponding electrode to be formed upon a subsequent layer. The fourth layer is formed at an offset position relative to the third layer, the second layer (first conductive strip 920), and the first layer. Subsequently, a fifth, non-conductive layer is formed above the conductive fourth layer. The fifth layer may also comprise a groove formation to accommodate the first via 915 as well as a second via 935 to be formed. Further, a sixth layer, comprising a third conductive strip 960 is formed above the fifth layer for electrical coupling with a corresponding electrode to be formed upon a subsequent layer. The sixth layer is formed at an offset position relative to the fifth layer, the fourth layer (second conductive strip 940), the third layer, the second layer (first conductive strip 920), and the first layer. A seventh, non-conductive layer is formed above this sixth layer. Three grooves are formed in the seventh layer to accommodate the first via 915, the second via 935 and a third via 955 to be formed.

Upon the seventh layer, a first electrode 910, a second electrode 930, and a third electrode 950 are formed. However, before the formation of the first through third electrodes, 910, 930, 950, the corresponding vias 915, 935, 955 are formed. The first via 915, that connects the first electrode 910 to the first conductive strip 920, is formed above the second layer and into the grooves that already exist in layers below the electrode, as discussed. Similarly, the second via 935 is formed above the fourth layer to connect the second electrode 930 with the second conductive strip 940. Further, the third via 955 is formed above the sixth layer and in the groove of the seventh layer below the third electrode. The third via 955 is capable of connecting the third electrode 950 to the third conductive strip 960. Therefore, all three electrodes 910, 930, 950, are respectively electrically coupled to the corresponding conductive strips 920, 940, 960. Due to the offsetting of the second, fourth, and sixth layers, both the conductive strips and the subsequently formed electrodes (in other words, the entire conducting structures) are offset from one another, such that all the electrodes are exposed on the surface of the electrode assembly. Further, similar techniques may be used to generate corresponding connection pads that connect to respective conductive strips, and hence to respective electrodes, thereby rendering the electrodes capable of electrical communications with an IMD.

The surface of the electrode assembly 210 is designed so that a conductive electrode is exposed only where it comes into contact with a portion of the patient's body, such that each individual electrode is electrically isolated from the other electrodes and from the conductive strips associated with the other electrodes. Therefore, independent signals may be sent to and from the electrodes 910, 930, 950 via the electrode assembly 210. In this manner, staggering of the time period relating to the delivery of stimulation signals is made possible. Further, independent acquisition of biometric data and delivery of an electrical signal may be performed substantially simultaneously. Utilizing the structure described in FIG. 8, the electrodes 910, 930, 950 are capable of operating independently. Although only three electrodes are illustrated in FIG. 8, those skilled in the art would appreciate that any number of electrodes may be implemented using the technique disclosed in FIG. 8 while still remaining within the spirit and scope of the present invention.

As seen in FIG. 8, all the electrodes 910, 930 and 950 are initially (i.e., prior to shaping the substrate into a helical form) formed to lie in a single plane or substantially in a single plane. In the arrangement illustrated in FIG. 8, this single plane or approximate single plane is the upper surface of the seventh layer. This plane is parallel or substantially parallel to the upper surface of the substrate, upon which the first layer is formed. The arrangement of FIG. 8, in which all the electrodes 910, 930 and 950 are initially formed to lie in a single plane, contrasts with the arrangements shown in FIGS. 6 and 7, in which the electrodes are initially formed in a staggered fashion, such that each electrode lies in a different plane, each of the different planes being parallel or substantially parallel to the upper surface of the substrate (substrate not shown in FIGS. 6 and 7) upon which the first layer is formed.

To be sure, in an arrangement such as any of the arrangements shown in FIGS. 6, 7 and 8, the electrodes may or may not be formed so as to lie in a single plane perpendicular to the upper surface of the substrate upon which the first layer is formed (that single plane would be the plane of the cross-section shown in FIGS. 7 and 8, i.e., the plane of the paper, or a plane parallel thereto). In FIGS. 6, 7 and 8, the electrodes are shown as in fact lying in such a single perpendicular plane, although this need not be the case.

Whether the electrodes are initially formed to lie in a single plane (parallel or perpendicular to the substrate) or in a staggered fashion, once the substrate is shaped into a helical form, the electrodes may lie in a straight line or in a staggered fashion, depending on the diameters of the coils of the helical form. The choice as to whether to make the electrodes lie in a straight line or in a staggered fashion in the finished electrode assembly will depend on the medical indications (e.g., as to where on the target tissue the electrodes should make contact) of the individual case in question for which the assembly is being prepared.

Utilizing embodiments of the present invention, an electrode assembly that comprises an array of electrodes may be deployed to perform various therapy delivery functions and/or sensing functions. Therefore, current steering and targeted delivery of therapeutic electrical signals to different portions of a particular nerve may be performed using the multi-electrode assembly described by embodiments of the present invention. Additionally, electrode assemblies provided by the embodiments of the present invention may be manufactured in a more uniform, dimensionally-controlled, and efficient manner utilizing process methods described herein and known to those skilled in the art of semiconductor manufacturing having benefit of the present disclosure. Embodiments of the present invention provide for more effective therapy and greater efficacy in delivering targeted therapy to various portions of the patient's body.

All of the methods and apparatuses disclosed and claimed herein may be made and executed without undue experimentation in light of the present disclosure. While the methods and apparatuses of this invention have been described in terms of particular embodiments, it will be apparent to those skilled in the art that variations may be applied to the methods and apparatuses and in the steps or in the sequence of steps of the methods described herein without departing from the concept, spirit, and scope of the invention, as defined by the appended claims. It should be especially apparent that the principles of the invention may be applied to selected cranial nerves other than the vagus nerve to achieve particular results.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed is:

1. A method for forming a helical electrode assembly for carrying a signal associated with an implantable medical device, comprising:

forming a first layer on a generally flat substrate;

forming a first conducting structure as a second layer upon said first layer, said second layer comprising a first electrode and a first conductive strip operatively coupled to said first electrode;

forming a third, non-conductive layer above said first and second layers;

forming a second conducting structure as a fourth layer upon said third layer, said fourth layer comprising a second electrode and a second conductive strip operatively coupled to said second electrode; and forming at least a portion of said generally flat substrate and the first, second, third and fourth layers into a helical structure, wherein forming said third layer comprises forming the third layer at an offset position on the second layer such that the third layer does not overlap the region in which the first electrode resides, such that a stair step of layers that contain electrodes and conductive strips is generated.

2. The method of claim 1, wherein forming said first and second conducting structures comprises:
performing a photolithography process to imprint said first conducting structure upon said first layer and said second conducting structure upon said third layer; and
performing an etch process to control at least one dimension relating to each of said first and second conducting structures within respective predetermined tolerances.

3. The method of claim 1, wherein forming said first and second conducting structures comprises:
performing a metal deposition process to deposit a conductive material for forming said first and second conducting structures; and
performing an etch process to control at least one dimension relating to each of said first and second conducting structures within predetermined tolerances.

4. The method of claim 1, further comprising:
forming a fifth, non-conducting layer above said third and fourth layers, and forming a third conducting structure as a sixth layer upon said fifth layer, said third conducting structure comprising a third electrode and a third conducting strip operatively coupled to said third electrode; and
forming a seventh non-conducting layer above said fifth and sixth layers, and forming a fourth conducting structure as an eighth layer upon said seventh layer, said fourth conducting structure comprising a fourth electrode and a fourth conducting strip operatively coupled to said fourth electrode.

5. The method of claim 1, further comprising:
forming a first connection pad on the surface of said electrode assembly, said first connection pad being electrically coupled to said first conductive strip; and
forming a second connection pad on the surface of said electrode assembly, said second connection pad being electrically coupled to said second conductive strip.

6. A method for forming a helical electrode assembly for carrying an electrical signal associated with an implantable medical device, comprising:
forming a plurality of layers on a generally flat substrate, including a first conducting structure and a second conducting structure as two of the plurality of layers; and
forming at least a portion of said generally flat substrate into a helical structure,
wherein said first conducting structure comprises a first electrode and a first conductive strip operatively coupled to said first electrode, and said second conducting structure comprises a second electrode and a second conductive strip operatively coupled to said second electrode,
wherein said first and second conducting structures are formed to be electrically isolated from one another, such that said first and second electrodes may be operated independently of one another, and
wherein forming said first and second conducting structures comprises offsetting said first conducting structure from said second conducting structure such that the second conducting structure does not overlap the region in which the first electrode resides, such that a stair step of layers that contain electrodes and conductive strips is generated.

7. The method of claim 6, wherein said first and second conducting structures are formed by (i) a photolithography process or a metal deposition process, and (ii) an etch process to control at least one dimension relating to each of said first and second conducting structures within respective predetermined tolerances.

8. The method of claim 7, further comprising performing a chemical-mechanical polishing process.

9. The method of claim 6, wherein said first and second conducting structures are formed to be electrically isolated from one another by forming a non-conductive layer therebetween.

10. The method of claim 6, wherein said plurality of layers comprises alternating non-conductive and conductive layers.

11. The method of claim 10, wherein said plurality of layers comprises four or more layers.

12. The method of claim 6, wherein said first and second electrodes are formed to lie on an interior surface of said helical structure, in a linear or staggered arrangement.

13. The method of claim 6, wherein said helical structure includes an elastomeric body portion comprising a material selected from the group consisting of silicone rubbers, siloxane polymers, polydimethylsiloxanes, polyurethane, polyether urethane, polyetherurethane urea, polyesterurethane, polyamide, polycarbonate, polyester, polypropylene, polyethylene, polystyrene, polyvinyl chloride, polytetrafluoroethylene, polysulfone, cellulose acetate, polymethylmethacrylate, polyethylene, and polyvinylacetate, and each of said first and second electrodes comprises a material selected from the group consisting of platinum, iridium, platinum/iridium alloys, and oxides thereof.

14. The method of claim 6, wherein said helical structure is coupled to a lead assembly via an interface, said lead assembly being coupled to the implantable medical device.

15. The method of claim 6, further comprising:
forming a first connection pad on the surface of said electrode assembly, said first connection pad being electrically coupled to said first conductive strip; and
forming a second connection pad on the surface of said electrode assembly, said second connection pad being electrically coupled to said second conductive strip.

16. The method of claim 6, further comprising:
forming a first via to electrically couple said first conductive strip to said first electrode; and
forming a second via to electrically couple said second conductive strip to said second electrode.

17. An electrode assembly for conducting electrical signals between an implantable medical device and a target tissue, comprising:
a helical member;
a first layer formed on the helical member;
a first conducting structure as a second layer formed upon said first layer, said second layer comprising a first electrode and a first conductive strip operatively coupled to said first electrode;
a third, non-conductive layer formed above said first and second layers;
a second conducting structure as a fourth layer formed upon said third layer, said fourth layer comprising a second electrode and a second conductive strip operatively coupled to said second electrode; and
wherein said third layer is formed at an offset position on the second layer such that the third layer does not overlap the region in which the first electrode resides, such that a stair step of layers that contain electrodes and conductive strips is generated.

18. The electrode assembly of claim 17, wherein said first and second conductive strips are positioned in at least a partially parallel configuration along the length of at least a portion of said helical member.

19. The electrode assembly of claim 17, further comprising a fifth, non-conductive layer formed above said first to fourth layers and a third conducting structure as a sixth layer formed upon said fifth layer, said sixth layer comprising a third electrode and a third conductive strip operatively coupled to said third electrode, wherein said first, second, and third electrodes form an electrode array.

20. The electrode assembly of claim 19, wherein said first electrode is adapted to carry a first electrical signal, said second electrode is adapted to carry a second electrical signal different from said first electrical signal, and said third electrode is adapted to carry a third electrical signal different from said first and second electrical signals.

21. The electrode assembly of claim 17, further comprising a first lead wire operatively coupled to said first conductive strip and a second lead wire operatively coupled to said second conductive strip.

22. The electrode assembly of claim 21, further comprising a lead interface operatively coupled to said helical member, said first and second lead wires being operatively coupled to said first and second conductive strips via said lead interface.

23. The electrode assembly of claim 17, wherein said helical material comprises a material selected from the group consisting of siloxane polymers, polydimethylsiloxanes, silicone rubbers, polyurethane, polyether urethane, polyetherurethane urea, polyesterurethane, polyamide, polycarbonate, polyester, polypropylene, polyethylene, polystyrene, polyvinyl chloride, polytetrafluoroethylene, polysulfone, cellulose acetate, polymethylmethacrylate, polyethylene, and polyvinylacetate, and said first and second electrodes comprises a material selected from the group consisting of platinum, iridium, and platinum/iridium alloys.

24. The electrode assembly of claim 17, wherein said helical member is capable of being wrapped around a nerve, wherein said first and second electrodes come into electrical contact with said nerve to deliver a stimulation signal in a cascading manner.

* * * * *